US012408853B2

(12) United States Patent
Kriscovich et al.

(10) Patent No.: US 12,408,853 B2
(45) Date of Patent: Sep. 9, 2025

(54) SMART BAG TO MEASURE URINE OUTPUT VIA CATHETER

(71) Applicant: C. R. Bard, Inc., Franklin Lakes, NJ (US)

(72) Inventors: Hannah Rose Kriscovich, Marietta, GA (US); Charles D. Shermer, Raleigh, NC (US); Puja Patel, Lawrenceville, GA (US); Shernone Moussignac, Conyers, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 754 days.

(21) Appl. No.: 17/552,250

(22) Filed: Dec. 15, 2021

(65) Prior Publication Data

US 2022/0192564 A1 Jun. 23, 2022

Related U.S. Application Data

(60) Provisional application No. 63/127,041, filed on Dec. 17, 2020.

(51) Int. Cl.
*A61B 5/20* (2006.01)
*A61B 5/00* (2006.01)
*A61B 90/00* (2016.01)

(52) U.S. Cl.
CPC ............ *A61B 5/208* (2013.01); *A61B 5/0002* (2013.01); *A61B 5/688* (2013.01); *A61B 90/06* (2016.02);
(Continued)

(58) Field of Classification Search
CPC ....... A61B 5/208; A61B 5/0002; A61B 5/688; A61B 90/06; A61B 2090/064;
(Continued)

(56) References Cited

U.S. PATENT DOCUMENTS 3,661,143 A 5/1972 Henkin
3,781,920 A 1/1974 Browne et al.
(Continued)

FOREIGN PATENT DOCUMENTS

CA 2882654 A1 10/2007
CN 2445749 Y 9/2001
(Continued)

OTHER PUBLICATIONS

Bard Medical, Criticore Disposables—Non I.C., 3 pages, www.bardmedical.com/products/patienl-moniloring-, ystems/criticore®-system/criticore®-disposables-non-ic/ Jan. 30, 2015.
(Continued)

*Primary Examiner* — Eric F Winakur
*Assistant Examiner* — Sienna C Pyle
(74) *Attorney, Agent, or Firm* — Rutan & Tucker LLP

(57) ABSTRACT

Disclosed herein is a urine collection bag, system, and methods directed to automated measurement of a quantity of urine. The urine collection system can include the urine collection bag, a catheter, and flexible drainage tubing. The urine collection bag can include a collection area, force sensors, and circuitry configured to determine the volume of urine in the collection area based on pressure or weight measured by the force sensors, and the specific gravity of the urine. The catheter may include a small female external catheter (FEC) with an opening on a top side, a wicking catheter with a wicking area on a top side, a finger-mountable catheter, or a male external catheter (MEC). The tubing may be secured to a patient's leg with a stabilization device or a fabric strap. The catheter can remain on a patient while the patient stands or walks.

25 Claims, 7 Drawing Sheets

(52) U.S. Cl.
CPC ... *A61B 2090/064* (2016.02); *A61B 2562/166* (2013.01)

(58) Field of Classification Search
CPC . A61B 2562/166; A61B 5/207; A61B 10/007; A61B 5/6801; G01N 33/493; A61M 2202/0496; A61M 2205/3331
See application file for complete search history.

(56) References Cited

U.S. PATENT DOCUMENTS

| | | | |
|---|---|---|---|
| 3,851,650 A | 12/1974 | Darling | |
| 3,919,455 A | 11/1975 | Sigdell et al. | |
| 4,276,889 A | 7/1981 | Kuntz et al. | |
| 4,286,590 A | 9/1981 | Murase | |
| 4,291,692 A | 9/1981 | Bowman et al. | |
| 4,296,749 A | 10/1981 | Pontifex | |
| 4,305,405 A | 12/1981 | Meisch | |
| 4,312,352 A | 1/1982 | Meisch et al. | |
| 4,343,316 A | 8/1982 | Jespersen | |
| 4,443,219 A | 4/1984 | Meisch et al. | |
| 4,448,207 A | 5/1984 | Parrish | |
| 4,509,366 A | 4/1985 | Matsushita et al. | |
| 4,532,936 A | 8/1985 | LeVeen et al. | |
| 4,658,834 A | 4/1987 | Blankenship et al. | |
| 4,712,567 A * | 12/1987 | Gille | A61B 5/14507 600/580 |
| 4,723,950 A | 2/1988 | Lee | |
| 4,834,706 A | 5/1989 | Beck et al. | |
| 4,850,375 A | 7/1989 | Rosenberg | |
| 4,889,532 A | 12/1989 | Metz et al. | |
| 5,002,541 A | 3/1991 | Conkling et al. | |
| 5,146,637 A | 9/1992 | Bressler et al. | |
| 5,409,014 A | 4/1995 | Napoli et al. | |
| 5,586,085 A | 12/1996 | Lichte | |
| 5,725,515 A | 3/1998 | Propp | |
| 5,733,319 A | 3/1998 | Neilson et al. | |
| 5,738,656 A | 4/1998 | Wagner | |
| 5,747,824 A | 5/1998 | Jung et al. | |
| 5,769,087 A | 6/1998 | Westphal et al. | |
| 5,807,278 A | 9/1998 | McRae | |
| 5,823,972 A | 10/1998 | McRae | |
| 5,891,051 A | 4/1999 | Han et al. | |
| 5,911,786 A | 6/1999 | Nielsen et al. | |
| 6,129,684 A | 10/2000 | Sippel et al. | |
| 6,132,407 A | 10/2000 | Genese et al. | |
| 6,250,152 B1 | 6/2001 | Klein et al. | |
| 6,256,532 B1 | 7/2001 | Cha | |
| 6,261,254 B1 | 7/2001 | Baron et al. | |
| 6,434,418 B1 | 8/2002 | Neal et al. | |
| 6,579,247 B1 | 6/2003 | Abramovitch et al. | |
| 6,592,612 B1 | 7/2003 | Samson et al. | |
| 6,709,420 B1 | 3/2004 | Lincoln et al. | |
| 6,716,200 B2 | 4/2004 | Bracken et al. | |
| 7,011,634 B2 | 3/2006 | Paasch et al. | |
| 7,161,484 B2 | 1/2007 | Tsoukalis | |
| 7,211,037 B2 | 5/2007 | Briggs et al. | |
| 7,437,945 B1 | 10/2008 | Feller | |
| 7,442,754 B2 | 10/2008 | Tepper et al. | |
| 7,739,907 B2 | 6/2010 | Boiarski | |
| 7,871,385 B2 | 1/2011 | Levinson | |
| 7,931,630 B2 | 4/2011 | Nishtala et al. | |
| 7,976,533 B2 | 7/2011 | Larsson | |
| 7,998,126 B1 | 8/2011 | Fernandez | |
| 8,295,933 B2 | 10/2012 | Gerber et al. | |
| 8,328,733 B2 | 12/2012 | Forte et al. | |
| 8,328,734 B2 | 12/2012 | Salvadori et al. | |
| 8,337,476 B2 | 12/2012 | Greenwald et al. | |
| 8,374,688 B2 | 2/2013 | Libbus et al. | |
| 8,403,884 B2 | 3/2013 | Nishtala | |
| 8,471,231 B2 | 6/2013 | Paz | |
| 8,663,128 B2 | 3/2014 | Paz et al. | |
| 8,773,259 B2 | 7/2014 | Judy et al. | |
| 8,790,277 B2 | 7/2014 | Elliott et al. | |
| 8,790,320 B2 | 7/2014 | Christensen | |
| 8,790,577 B2 | 7/2014 | Mizumoto et al. | |
| 8,813,551 B2 | 8/2014 | Boiarski | |
| 8,827,924 B2 | 9/2014 | Paz et al. | |
| 8,832,558 B2 | 9/2014 | Cardarelli et al. | |
| 8,900,196 B2 | 12/2014 | Andino | |
| 9,045,887 B2 | 6/2015 | O'Malley | |
| 9,050,046 B2 | 6/2015 | Elliott et al. | |
| 9,074,920 B2 | 7/2015 | Mendels et al. | |
| 9,216,242 B2 | 12/2015 | Nishtala et al. | |
| 9,480,821 B2 | 11/2016 | Ciccone et al. | |
| 9,592,034 B2 | 3/2017 | Hall et al. | |
| 9,642,987 B2 | 5/2017 | Bierman et al. | |
| 9,731,097 B2 * | 8/2017 | Andino | A61M 25/02 |
| 9,895,095 B2 | 2/2018 | Chen | |
| 9,962,516 B2 | 5/2018 | Lampotang et al. | |
| 10,071,202 B2 | 9/2018 | Handler | |
| 10,182,747 B2 | 1/2019 | Charlez et al. | |
| 10,245,008 B2 | 4/2019 | Paige | |
| 10,362,981 B2 | 7/2019 | Paz et al. | |
| 10,383,606 B1 | 8/2019 | McCord et al. | |
| 10,448,875 B2 | 10/2019 | Holt et al. | |
| 10,799,386 B1 * | 10/2020 | Harrison, Sr. | A61F 5/441 |
| 10,881,778 B2 | 1/2021 | Scarpaci et al. | |
| 11,540,760 B1 | 1/2023 | Guillemette | |
| 11,703,365 B2 | 7/2023 | Tourchak et al. | |
| 12,109,353 B2 | 10/2024 | Cheng et al. | |
| 2001/0056226 A1 | 12/2001 | Zodnik et al. | |
| 2002/0016719 A1 | 2/2002 | Nemeth et al. | |
| 2002/0161314 A1 | 10/2002 | Sarajarvi | |
| 2002/0193760 A1 | 12/2002 | Thompson | |
| 2003/0000303 A1 | 1/2003 | Livingston et al. | |
| 2003/0163183 A1 | 8/2003 | Carson | |
| 2003/0163287 A1 | 8/2003 | Vock et al. | |
| 2004/0267086 A1 | 12/2004 | Anstadt et al. | |
| 2005/0020958 A1 | 1/2005 | Paolini et al. | |
| 2005/0065583 A1 | 3/2005 | Voorhees et al. | |
| 2005/0172712 A1 | 8/2005 | Nyce | |
| 2005/0247121 A1 | 11/2005 | Pelster | |
| 2006/0065713 A1 | 3/2006 | Kingery | |
| 2006/0100743 A1 | 5/2006 | Townsend et al. | |
| 2006/0253091 A1 * | 11/2006 | Vernon | A61F 5/44 604/323 |
| 2007/0010797 A1 | 1/2007 | Nishtala et al. | |
| 2007/0078444 A1 | 4/2007 | Larsson | |
| 2007/0106177 A1 * | 5/2007 | Hama | G01G 17/04 600/573 |
| 2007/0145137 A1 | 6/2007 | Mrowiec | |
| 2007/0225668 A1 | 9/2007 | Otto | |
| 2007/0252714 A1 | 11/2007 | Rondoni et al. | |
| 2008/0027409 A1 | 1/2008 | Rudko et al. | |
| 2008/0217391 A1 | 9/2008 | Roof et al. | |
| 2008/0312550 A1 | 12/2008 | Nishtala et al. | |
| 2008/0312556 A1 | 12/2008 | Dijkman | |
| 2009/0056020 A1 | 3/2009 | Caminade et al. | |
| 2009/0099629 A1 | 4/2009 | Carson et al. | |
| 2009/0157430 A1 | 6/2009 | Rule et al. | |
| 2009/0287170 A1 | 11/2009 | Otto | |
| 2009/0315684 A1 | 12/2009 | Sacco et al. | |
| 2010/0064426 A1 | 3/2010 | Chikara Imamura | |
| 2010/0094204 A1 | 4/2010 | Nishtala | |
| 2010/0130949 A1 | 5/2010 | Garcia | |
| 2010/0137743 A1 | 6/2010 | Nishtala et al. | |
| 2011/0113540 A1 | 5/2011 | Plate et al. | |
| 2011/0120219 A1 | 5/2011 | Barlesi et al. | |
| 2011/0178425 A1 | 7/2011 | Nishtala et al. | |
| 2011/0224636 A1 | 9/2011 | Keisic | |
| 2011/0230824 A1 | 9/2011 | Salinas et al. | |
| 2011/0238042 A1 | 9/2011 | Davis et al. | |
| 2011/0251572 A1 | 10/2011 | Nishtala et al. | |
| 2011/0263952 A1 | 10/2011 | Bergman et al. | |
| 2012/0029408 A1 | 2/2012 | Beaudin | |
| 2012/0035496 A1 | 2/2012 | Denison et al. | |
| 2012/0059286 A1 | 3/2012 | Hastings et al. | |
| 2012/0078137 A1 | 3/2012 | Mendels et al. | |
| 2012/0078235 A1 | 3/2012 | Martin et al. | |
| 2012/0095304 A1 | 4/2012 | Biondi | |
| 2012/0109008 A1 | 5/2012 | Charlez et al. | |
| 2012/0118650 A1 | 5/2012 | Gill | |
| 2012/0123233 A1 | 5/2012 | Cohen | |

(56) References Cited

U.S. PATENT DOCUMENTS

| | | |
|---|---|---|
| 2012/0127103 A1 | 5/2012 | Qualey et al. |
| 2012/0226196 A1 | 9/2012 | DiMino et al. |
| 2012/0234434 A1 | 9/2012 | Woodruff et al. |
| 2012/0302917 A1 | 11/2012 | Fitzgerald et al. |
| 2012/0323144 A1 | 12/2012 | Coston et al. |
| 2012/0323502 A1 | 12/2012 | Tanoura et al. |
| 2013/0066166 A1 | 3/2013 | Burnett et al. |
| 2013/0109927 A1 | 5/2013 | Menzel |
| 2013/0109928 A1 | 5/2013 | Menzel |
| 2013/0131610 A1 | 5/2013 | Dewaele et al. |
| 2013/0218106 A1 | 8/2013 | Coston et al. |
| 2013/0245498 A1 | 9/2013 | Delaney et al. |
| 2013/0267871 A1 | 10/2013 | Delaney et al. |
| 2014/0039348 A1 | 2/2014 | Bullington et al. |
| 2014/0155781 A1 | 6/2014 | Bullington et al. |
| 2014/0155782 A1 | 6/2014 | Bullington et al. |
| 2014/0159921 A1 | 6/2014 | Qualey et al. |
| 2014/0187666 A1 | 7/2014 | Aizenberg et al. |
| 2014/0207085 A1 | 7/2014 | Brandt et al. |
| 2014/0243635 A1 | 8/2014 | Arefieg |
| 2014/0335490 A1 | 11/2014 | Baarman et al. |
| 2015/0120321 A1 | 4/2015 | David et al. |
| 2015/0233749 A1 | 8/2015 | Wang et al. |
| 2015/0342576 A1 | 12/2015 | Hall et al. |
| 2015/0343173 A1 | 12/2015 | Tobescu et al. |
| 2015/0359522 A1 | 12/2015 | Recht et al. |
| 2015/0362351 A1 | 12/2015 | Joshi et al. |
| 2016/0051176 A1* | 2/2016 | Ramos ............... G01F 23/265 600/573 |
| 2016/0183819 A1 | 6/2016 | Burnett et al. |
| 2017/0035342 A1 | 2/2017 | Elia et al. |
| 2017/0043089 A1 | 2/2017 | Handler |
| 2017/0100068 A1 | 4/2017 | Kostov |
| 2017/0113000 A1 | 4/2017 | Tobescu et al. |
| 2017/0136209 A1 | 5/2017 | Burnett et al. |
| 2017/0140103 A1* | 5/2017 | Angelides ............. A61F 5/4404 |
| 2017/0196478 A1 | 7/2017 | Hunter |
| 2017/0202698 A1 | 7/2017 | Zani et al. |
| 2017/0249445 A1 | 8/2017 | Devries et al. |
| 2017/0290540 A1 | 10/2017 | Franco |
| 2017/0291012 A1 | 10/2017 | Iglesias |
| 2017/0307423 A1 | 10/2017 | Pahwa et al. |
| 2017/0322197 A1 | 11/2017 | Hall et al. |
| 2018/0015251 A1 | 1/2018 | Lampotang et al. |
| 2018/0110456 A1 | 4/2018 | Cooper et al. |
| 2018/0160961 A1 | 6/2018 | Gopinathan et al. |
| 2018/0214122 A1 | 8/2018 | Ansell et al. |
| 2018/0214297 A1 | 8/2018 | Hughett et al. |
| 2018/0245967 A1 | 8/2018 | Parker et al. |
| 2018/0280236 A1 | 10/2018 | Ludin et al. |
| 2018/0317891 A1 | 11/2018 | Kim |
| 2018/0344234 A1 | 12/2018 | Mckinney et al. |
| 2019/0006047 A1* | 1/2019 | Gorek ................... G06F 18/25 |
| 2019/0017535 A1 | 1/2019 | Ormsbee et al. |
| 2019/0046102 A1 | 2/2019 | Kushnir et al. |
| 2019/0069829 A1 | 3/2019 | Bulut |
| 2019/0069830 A1 | 3/2019 | Holt et al. |
| 2019/0126006 A1 | 5/2019 | Rehm et al. |
| 2019/0150821 A1 | 5/2019 | Waters et al. |
| 2019/0167144 A1 | 6/2019 | Jung et al. |
| 2019/0201596 A1 | 7/2019 | Luxon et al. |
| 2019/0223844 A1 | 7/2019 | Aboagye et al. |
| 2019/0247236 A1 | 8/2019 | Sides et al. |
| 2019/0254582 A1 | 8/2019 | Wei et al. |
| 2019/0321588 A1 | 10/2019 | Burnett et al. |
| 2019/0328945 A1 | 10/2019 | Analytis et al. |
| 2019/0343445 A1 | 11/2019 | Burnett et al. |
| 2019/0358387 A1 | 11/2019 | Elbadry et al. |
| 2019/0365308 A1 | 12/2019 | Laing et al. |
| 2019/0381223 A1 | 12/2019 | Culbert et al. |
| 2020/0022637 A1 | 1/2020 | Kurzrock et al. |
| 2020/0064172 A1 | 2/2020 | Tabaczewski et al. |
| 2020/0085378 A1 | 3/2020 | Burnett et al. |
| 2020/0187863 A1 | 6/2020 | Tu et al. |
| 2020/0268302 A1 | 8/2020 | Oh |
| 2020/0268303 A1 | 8/2020 | Oliva |
| 2020/0289749 A1 | 9/2020 | Odashima et al. |
| 2020/0405524 A1 | 12/2020 | Gill |
| 2021/0054610 A1 | 2/2021 | Hall et al. |
| 2021/0077007 A1 | 3/2021 | Jouret et al. |
| 2021/0100533 A1 | 4/2021 | Seres et al. |
| 2021/0299353 A1 | 9/2021 | Mannu et al. |
| 2022/0018692 A1 | 1/2022 | Tourchak et al. |
| 2022/0026001 A1 | 1/2022 | Cheng et al. |
| 2022/0026261 A1 | 1/2022 | Funnell et al. |
| 2022/0079487 A1 | 3/2022 | Horiguchi et al. |
| 2022/0192565 A1 | 6/2022 | Cheng et al. |
| 2022/0192566 A1 | 6/2022 | Cheng et al. |
| 2022/0193375 A1 | 6/2022 | Rehm et al. |
| 2022/0233120 A1 | 7/2022 | Beuret et al. |
| 2022/0296140 A1 | 9/2022 | Nguyen et al. |
| 2022/0330867 A1 | 10/2022 | Conley et al. |
| 2022/0386917 A1 | 12/2022 | Mann et al. |
| 2023/0019703 A1 | 1/2023 | Behzad et al. |
| 2023/0022547 A1 | 1/2023 | Cho et al. |
| 2023/0025333 A1 | 1/2023 | Patel et al. |
| 2023/0028966 A1 | 1/2023 | Franano |
| 2023/0035669 A1 | 2/2023 | Raja et al. |
| 2023/0040915 A1 | 2/2023 | Compton et al. |
| 2023/0058553 A1 | 2/2023 | Fallows et al. |
| 2023/0060232 A1 | 3/2023 | Patel et al. |
| 2023/0084476 A1 | 3/2023 | Robichaud et al. |
| 2023/0089041 A1 | 3/2023 | Handler |
| 2024/0042120 A1 | 2/2024 | Cheng et al. |
| 2024/0081708 A1 | 3/2024 | Kelly et al. |
| 2024/0108268 A1 | 4/2024 | Woodard et al. |
| 2024/0252783 A1 | 8/2024 | Waitkus et al. |
| 2024/0347162 A1 | 10/2024 | Meese et al. |
| 2024/0360938 A1 | 10/2024 | Cheng et al. |
| 2024/0424186 A1 | 12/2024 | Justice et al. |
| 2025/0090066 A1 | 3/2025 | Tourchak |
| 2025/0120636 A1 | 4/2025 | Compton et al. |
| 2025/0205456 A1 | 6/2025 | Rehm et al. |

FOREIGN PATENT DOCUMENTS

| | | | |
|---|---|---|---|
| CN | 200951235 Y | | 9/2007 |
| CN | 201492414 U | | 6/2010 |
| CN | 102647939 A | | 8/2012 |
| CN | 103054559 B | | 5/2015 |
| CN | 107952140 A | * | 4/2018 |
| CN | 109498013 A | | 3/2019 |
| CN | 110859636 A | | 3/2020 |
| CN | 112426156 A | | 3/2021 |
| EP | 0342028 A2 | | 11/1989 |
| ES | 2760470 T3 | | 5/2020 |
| GB | 2437549 A | | 10/2007 |
| GB | 2576743 A | | 3/2020 |
| JP | S49-75171 A | | 7/1974 |
| JP | S54-147066 A | | 11/1979 |
| JP | S58-190719 A | | 11/1983 |
| JP | S60-219517 A | | 11/1985 |
| JP | H02-057240 B2 | | 12/1990 |
| JP | H08-271301 A | | 10/1996 |
| JP | H10-104041 A | | 4/1998 |
| JP | 2007-303982 A | | 11/2007 |
| JP | 2008-524618 A | | 7/2008 |
| JP | 2009-068959 A | | 4/2009 |
| JP | 2010-121950 A | | 6/2010 |
| JP | 2010-530978 A | | 9/2010 |
| JP | 2012-105947 A | | 6/2012 |
| JP | 2012-225790 A | | 11/2012 |
| JP | 2018108356 A | | 7/2018 |
| KR | 20070115495 A | | 12/2007 |
| NL | 2013740 A | | 8/2016 |
| RU | 2615727 C2 | | 4/2017 |
| WO | 1981003427 A1 | | 12/1981 |
| WO | 2004045410 A1 | | 6/2004 |
| WO | 2013013782 A2 | | 1/2013 |
| WO | 20130178742 A1 | | 12/2013 |
| WO | 2014/043650 A2 | | 3/2014 |
| WO | 2014105755 A1 | | 7/2014 |
| WO | 2014108690 A1 | | 7/2014 |
| WO | 2014/135856 A1 | | 9/2014 |

(56) References Cited

FOREIGN PATENT DOCUMENTS

| | | | |
|---|---|---|---|
| WO | 2014/151068 A2 | 9/2014 |
| WO | 2014145971 A2 | 9/2014 |
| WO | 201511402 A1 | 1/2015 |
| WO | 2015/105916 A1 | 7/2015 |
| WO | 2015/127390 A1 | 8/2015 |
| WO | 2015191125 A1 | 12/2015 |
| WO | 2016177901 A1 | 11/2016 |
| WO | 2017/023794 A1 | 2/2017 |
| WO | 2018156624 A1 | 8/2018 |
| WO | 2019066357 A1 | 4/2019 |
| WO | 2019106675 A1 | 6/2019 |
| WO | 2019/226697 A1 | 11/2019 |
| WO | 2020033752 A1 | 2/2020 |
| WO | 2020154370 A1 | 7/2020 |
| WO | 2022108589 A1 | 5/2022 |
| WO | 2022182794 A1 | 9/2022 |
| WO | 2023022895 A1 | 2/2023 |
| WO | 2023027871 A1 | 3/2023 |
| WO | 2023076067 A1 | 5/2023 |

OTHER PUBLICATIONS

Bard Medical, Criticore Infection Control Disposables, 3 pages, www.bardmedical.com/patienl-moniloring-,ystems/criticore®-system/criticore®-infection-control-disposables/ Jan. 30, 2015.

Bard Medical, Criticore Monitor, 11 pages, www.bardmedical.com/products/patient-monitoring-systems/criticore®--monitor/ Jan. 30, 2015.

Bard Medical, Urine Meiers, 3 pages, www.bardmedical.com/products/urological-drainage/urine-collection/urinemeters/Jan. 30, 2015.

Biometrix, Urimetrix, 4 pages, www.biometrixmedical.com/Products/56/Urimetrix%E2%84%A2 Oct. 29, 2014.

Observe Medical, sippi, 3 pages, www.observemedical.com/products.html Oct. 29, 2014.

PCT/US19/33389 filed May 21, 2019 International Search Report and Written Opinion dated Aug. 2, 2019.

PCT/US2016/044835 filed Jul. 20, 2016 International Search Report and Written Opinion dated Dec. 16, 2016.

U.S. Appl. No. 17/054,493, filed Nov. 10, 2020 Final Office Action dated May 31, 2022.

U.S. Appl. No. 15/748,107, filed Jan. 26, 2018 Final Office Action dated Dec. 23, 2020.

U.S. Appl. No. 15/748,107, filed Jan. 26, 2018 Final Office Action dated Feb. 7, 2022.

U.S. Appl. No. 15/748,107, filed Jan. 26, 2018 Non-Final Office Action dated Sep. 3, 2021.

U.S. Appl. No. 15/748,107, filed Jan. 26, 2018 Non-Final Office Action dated Sep. 4, 2020.

U.S. Appl. No. 17/054,493, filed Nov. 10, 2020 Non-Final Office Action dated Nov. 24, 2021.

DFree Personal—Consumer Product Brochure, 2019.

DFree Pro Brochure 2019.

Leonhäuser, D et al., "Evaluation of electrical impedance tomography for determination of urinary bladder volume: comparison with standard ultrasound methods in healthy volunteers."—BioMed Engr On-line; 17:95; 2018.

Li, R., et al., "Design of a Noninvasive Bladder Urinary vol. Monitoring System Based on Bio-Impedance."—Engineering; vol. 5; pp. 321-325; 2013.

Reichmuth, M., et al., "A Non-invasive Wearable Bioimpedance System to Wirelessly Monitor Bladder Filling."—Dep. of Health Sciences and Technology—Department of Information Technology and Electrical Engineering ETH Zurich, Zurich, Switzerland—Conference Paper; Mar. 2020.

SECA product catalog, https://US.secashop.com/products/seca-mbca/seca-mbca-514/5141321139, last accessed Sep. 11, 2020.

U.S. Appl. No. 17/054,493, filed Nov. 10, 2020 Final Office Action dated Oct. 4, 2023.

U.S. Appl. No. 17/262,080, filed Jan. 21, 2021 Final Office Action dated Sep. 11, 2023.

U.S. Appl. No. 17/262,080, filed Jan. 21, 2021 Notice of Allowance dated Oct. 13, 2023.

U.S. Appl. No. 17/306,821, filed May 3, 2021 Advisory Action dated Oct. 3, 2023.

U.S. Appl. No. 17/373,546, filed Jul. 12, 2021 Non-Final Office Action dated Nov. 1, 2023.

EP 20962628.2 filed May 31, 2023 Extended European Search Report dated Apr. 20, 2024.

EP 23188337.2 filed May 21, 2019 Extended European Search Report dated Dec. 4, 2023.

PCT/US2019/033389 filed Nov. 26, 2020 Extended European Search Report dated Jun. 4, 2021.

PCT/US2022/039191 filed Aug. 2, 2022 International Search Report and Written Opinion dated Dec. 5, 2022.

PCT/US2022/039746 filed Aug. 8, 2022 International Search Report and Written Opinion dated Nov. 18, 2022.

PCT/US2022/046920 filed Oct. 17, 2022 International Search Report and Written Opinion dated Feb. 20, 2023.

U.S. Appl. No. 17/054,493, filed Nov. 10, 2020 Notice of Allowance dated Jan. 4, 2024.

U.S. Appl. No. 17/306,821, filed May 3, 2021 Notice of Allowance dated Apr. 23, 2024.

U.S. Appl. No. 17/373,546, filed Jul. 12, 2021 Notice of Allowance dated Mar. 7, 2024.

U.S. Appl. No. 17/373,546, filed Jul. 12, 2021 Notice of Allowance dated May 29, 2024.

U.S. Appl. No. 17/556,907, filed Dec. 20, 2021 Notice of Allowance dated Dec. 6, 2023.

U.S. Appl. No. 17/556,931, filed Dec. 20, 2021 Non-Final Office Action dated Mar. 27, 2024.

U.S. Appl. No. 17/556,931, filed Dec. 20, 2021 Restriction Requirement dated Feb. 22, 2024.

PCT/US2019/045787 filed Aug. 8, 2019 International Preliminary Report on Patentability dated Feb. 16, 2021.

PCT/US2019/045787 filed Aug. 8, 2019 International Search Report and Written Opinion dated Oct. 2, 2019.

PCT/US20/61367 filed Nov. 19, 2020 International Search Report and Written Opinion dated Feb. 22, 2021.

U.S. Appl. No. 17/262,080, filed Jan. 21, 2021 Non-Final Office Action dated Apr. 6, 2023.

U.S. Appl. No. 17/373,535, filed Jul. 12, 2021 Notice of Allowance dated Feb. 23. 2023.

U.S. Appl. No. 17/556,907, filed Dec. 20, 2021 Restriction Requirement dated May 12, 2023.

U.S. Appl. No. 15/748,107, filed Jan. 26, 2018 Notice of Allowance dated Dec. 12, 2022.

U.S. Appl. No. 17/054,493, filed Nov. 10, 2020 Non-Final Office Action dated Jan. 27, 2023.

U.S. Appl. No. 17/3026,821, filed May 3, 2021 Non-Final Office Action dated Jan. 10, 2023.

U.S. Appl. No. 17/373,535, filed Jul. 12, 2021 Non-Final Office Action dated Nov. 9. 2022.

"Urocare Reusable Night Drain Bottle—Urinary Collection System" Aug. 13, 2020, HealthProductsForYou.com, <https://www.healthproductsforyou.com/p-urocare-reusable-night-drain-bottle-urinary-collection-system.html> retrieved from Archive.org (Year: 2020).

U.S. Appl. No. 17/556,931, filed Dec. 20, 2021 Advisory Action dated Dec. 6, 2024.

U.S. Appl. No. 17/556,931, filed Dec. 20, 2021 Final Office Action dated Oct. 1, 2024.

U.S. Appl. No. 17/560,079, filed Dec. 22, 2021 Notice of Allowance dated Oct. 29. 2024.

PCT/US2022/017574 filed Feb. 23, 2022 Internation Search Report and Written Opinion dated Jun. 8, 2022.

Schlebusch, T. et al., "Bladder volume estimation from electrical impedance tomography" Physiological Measurement Institute of Physics Publishing, Bristol, GB. vol. 35 No. 9 Aug. 20, 2014. (Aug. 20, 2014).

U.S. Appl. No. 17/306,821, filed May 3, 2021 Final Office Action dated Jul. 19, 2023.

U.S. Appl. No. 17/556,907, filed Dec. 20, 2021 Non-Final Office Action dated Aug. 17, 2023.

(56) References Cited

OTHER PUBLICATIONS

"Volumetric Flow Rate", www.vcalc.com/wiki/JeffNolumetric+%28Fluid%29+Flow+Rate, accessed Jan. 9, 2025, created Mar. 8, 2018 (Year: 2018).
U.S. Appl. No. 17/556,931, filed Dec. 20, 2021 Notice of Allowance dated Mar. 18, 2025.
U.S. Appl. No. 17/587,938, filed Jan. 28, 2022 Restriction Requirement dated Jan. 22, 2025.
U.S. Appl. No. 17/833,682, filed Jun. 6, 2022 Non-Final Office Action dated Jan. 15, 2025.
U.S. Appl. No. 17/870,698, filed Jul. 21, 2022 Restriction Requirement dated Feb. 12, 2025.
U.S. Appl. No. 17/879,658, filed Aug. 2, 2022 Non-Final Office Action dated Dec. 30, 2024.
U.S. Appl. No. 17/893,435, filed Aug. 23, 2022 Non-Final Office Action dated Jan. 17, 2025.
U.S. Appl. No. 17/587,938 filed Jan. 28, 2022 Non-Final Office Action dated May 12, 2025.
U.S. Appl. No. 17/682,785 filed Feb. 28, 2022 Restriction Requirement dated Apr. 2, 2025.
U.S. Appl. No. 17/833,682 filed Jun. 6, 2022 Final Office Action dated May 12, 2025.
U.S. Appl. No. 17/863,223 filed Jul. 12, 2022 Non-Final Office Action dated Apr. 2, 2025.
U.S. Appl. No. 17/870,698 filed Jul. 21, 2022 Non-Final Office Action dated Apr. 9, 2025.
U.S. Appl. No. 18/278,167 filed Aug. 21, 2023 Non-Final Office Action dated Apr. 24, 2025.
U.S. Appl. No. 17/863,923 filed Jul. 13, 2022 Restriction Requirement dated May 21, 2025.
U.S. Appl. No. 17/873,834 filed Jul. 26, 2022 Non-Final Office Action dated May 19, 2025.
U.S. Appl. No. 17/879,658 filed Aug. 2, 2022 Final Office Action dated May 14, 2025.
U.S. Appl. No. 17/883,507 filed Aug. 8, 2022 Restriction Requirement dated May 19, 2025.
U.S. Appl. No. 17/941,941 filed Sep. 9, 2022 Restriction Requirement dated May 28, 2025.
U.S. Appl. No. 18/036,335 filed May 10, 2023 Non-Final Office Action dated Jun. 18, 2025.
U.S. Appl. No. 18/682,075 filed Feb. 7, 2024 Non-Final Office Action dated Jun. 18, 2025.

* cited by examiner

SMART BAG TO MEASURE URINE OUTPUT VIA CATHETER

PRIORITY

This application claims the benefit of priority to U.S. Provisional Application No. 63/127,041, filed Dec. 17, 2020, which is incorporated by reference in its entirety into this application.

SUMMARY

Briefly summarized, embodiments disclosed herein are directed to systems, methods and apparatuses for automated measurement of a quantity of urine.

One problem that often arises with collecting urine output (UO) data so clinicians can monitor and adjust the dosage of diuretics given to ambulatory patients is that conventional methods for collecting UO data (such as urine hats, bedside commodes, or bedpans) require patient compliance to urinate in the correct place. In many cases, patients are unable or unwilling to comply meticulously with their clinicians' instructions, or simply become fatigued or forget to comply as time goes on.

A second problem is that conventional methods of collecting UO data require valuable clinical time to read and record the data accurately. For example, a nurse or other clinician may visually measure the amount of UO in a collection container like a urine hat, which consumes time and may be prone to human error. In addition, the clinician must record the data at regular intervals, for example every hour, in order to record a time series of UO measurements. This consumes additional valuable clinical time, while also increasing the chance of human error.

A third problem is that indwelling Foley catheters, another option to accurately collect UO, can put patients at increased risk of catheter-associated urinary tract infections (CAUTIs). CAUTIs can lead to potentially dangerous complications, which can increase morbidity and even mortality in some cases, as well as causing discomfort and increasing treatment costs.

Disclosed herein is a urine collection bag that can address these problems. The urine collection bag includes a collection area configured to collect urine received via tubing from a catheter. The urine collection bag further includes one or more force sensors coupled to or integrated into the urine collection bag. The one or more force sensors are configured to measure a pressure or a weight of the urine collected within the collection area. The urine collection bag further includes circuitry configured to determine the amount of the urine based at least on the pressure or weight measured by the one or more force sensors, and a specific gravity of the urine.

In some embodiments, while determining the amount of the urine, the circuitry is further configured to determine that the pressure or weight measured by the one or more force sensors remains substantially constant for a predetermined time period. The circuitry is further configured to divide the pressure or weight by the specific gravity of the urine to determine an increase of a volume of the urine.

In some embodiments, the circuitry receives the specific gravity of the urine as an input via a user interface.

In some embodiments, the one or more force sensors comprise a resistive element operative to change resistance in response to a force. The resistance is measured by a printed circuit board (PCB).

In some embodiments, the PCB further comprises a low-pass filter operative to filter noise.

In some embodiments, the one or more force sensors comprise a plurality of force sensors.

In some embodiments, the collection area comprises a flexible pouch. The one or more force sensors measure the pressure of the urine by measuring an expansive force of the urine on one or more side walls of the flexible pouch.

In some embodiments, the one or more force sensors are situated in an internal layer of the one or more side walls of the flexible pouch.

In some embodiments, the catheter includes one or more of a small female external catheter (FEC) with an opening disposed on a top side, the opening configured to couple to a female anatomical part, a wicking catheter having a wicking area disposed on a top side, a finger-mountable catheter having a finger cavity configured to receive a user finger on a bottom side of the finger-mountable catheter, or a male external catheter (MEC).

In some embodiments, the catheter is configured to remain on a patient while the patient stands or walks.

In some embodiments, the urine collection bag further comprises a wireless transmitter configured to transmit the determined amount of the urine to an electronic medical records system.

In some embodiments, the circuitry comprises a printed circuit board (PCB) or a processor.

In some embodiments, a respective force sensor of the one or more force sensors is powered by a battery.

Also disclosed herein is a urine collection system. The urine collection system comprises a catheter, a urine collection bag configured to measure an amount of urine, and flexible drainage tubing coupling the catheter to the urine collection bag. The urine collection bag comprises a collection area configured to collect the urine, wherein the urine is received via the flexible drainage tubing from the catheter. The urine collection bag further comprises one or more force sensors coupled to or integrated into the urine collection bag. The one or more force sensors are configured to measure a pressure or a weight of the urine collected within the collection area. The urine collection bag further comprises circuitry configured to determine the amount of the urine based at least on the pressure or weight measured by the one or more force sensors, and a specific gravity of the urine.

In some embodiments, the flexible drainage tubing is secured to a leg of a patient with a stabilization device comprising an adhesive pad, the adhesive pad comprising one or more adhesive wings, and a retainer configured to stabilize the flexible drainage tubing. Alternatively, the flexible drainage tubing is secured to a leg of a patient with a fabric strap wrapped around the leg.

In some embodiments, the urine collection system further comprises a wireless transmitter configured to transmit the determined amount of the urine to an electronic medical records system.

Also disclosed herein is a method of using a urine collection bag and a catheter to measure an amount of urine. The method comprises receiving the urine, by the urine collection bag, via tubing from the catheter. The method further comprises collecting the urine, by the urine collection bag, in a collection area of the urine collection bag. The method further comprises measuring, by one or more force sensors coupled to or integrated into the urine collection bag, a pressure or a weight of the urine collected within the collection area. The method further comprises determining the amount of the urine, by circuitry coupled to or integrated into the urine collection bag, and based at least on the pressure or weight measured by the one or more force sensors, and a specific gravity of the urine.

In some embodiments, the tubing connecting the catheter to the urine collection bag is secured to a leg of the patient with a stabilization device. The stabilization device comprises an adhesive pad comprising one or more adhesive wings and a retainer configured to stabilize the flexible drainage tubing. Alternatively, the tubing connecting the catheter to the urine collection bag is secured to a leg of the patient with a fabric strap wrapped around the leg.

In some embodiments, the catheter is configured to remain on the patient while the patient stands or walks.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which.

DETAILED DESCRIPTION

Figure 1:
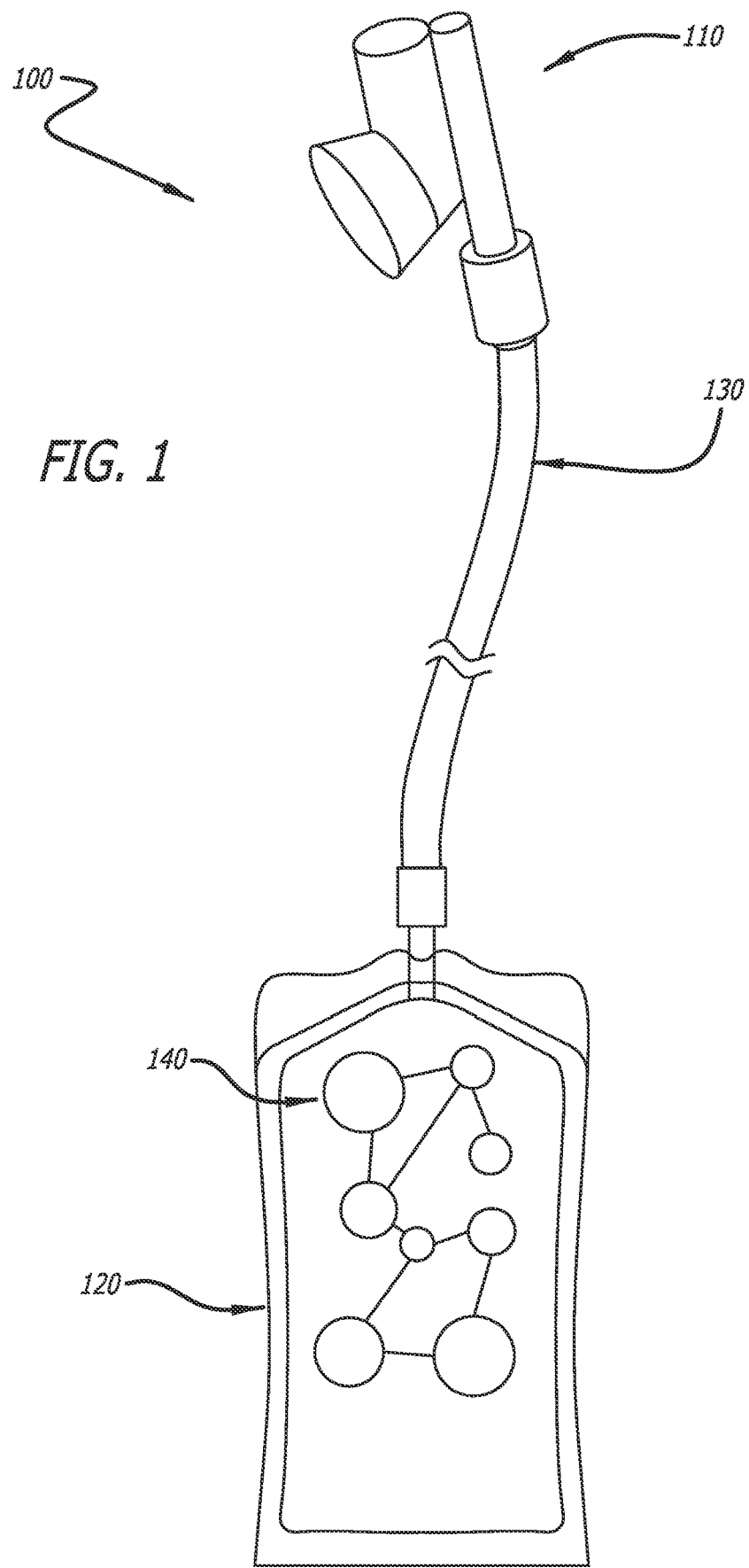
FIG. 1 illustrates a urine collection system, according to some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Clinicians often require accurate urine output (UO) data in order to monitor and adjust the dosage of diuretics given to ambulatory patients. Conventional methods for collecting UO data include urine hats, bedside commodes, and bedpans. However, these methods require patient compliance to urinate in the correct place. These methods also consume valuable clinician time to accurately read and record the data. Another existing option to accurately collect UO is indwelling Foley catheters. However, such indwelling catheters can put patients at increased risk of catheter-associated urinary tract infections (CAUTIs).

The disclosed urine collection system and methods can address these problems by automating accurate measurement of UO while a patient sits, stands, walks, and goes about other activities. As a result, the disclosed system and methods can measure UO more continually and accurately than conventional systems, while also being less disruptive to patients' lives.

Referring to FIG. 1, a urine collection system 100 is illustrated, according to some embodiments. System 100 includes a catheter 110, a urine collection bag 120 that can measure the weight and/or volume of urine it contains, and tubing 130 coupling catheter 110 to urine collection bag 120. The urine collection bag 120 comprises a collection area configured to collect the urine received via tubing 130. In an embodiment, the urine collection bag 120 may be inside a rigid container supporting the bottom and/or side walls of collection bag 120. Alternatively, the urine collection bag 120 may attach to a wheelchair, a bed, or a patient's leg.

The urine collection bag 120 further comprises a network of force sensors 140, which are coupled to or integrated into collection bag 120. The force sensors 140 can measure forces, pressure, or weight of the urine in the collection area. The urine collection bag 120 can also include circuitry that can compute the amount of urine based on the pressure or weight measured by the network of force sensors 140, taking into account information about the urine's specific gravity. For example, system 100 can determine the volume of urine contained in urine collection bag 120 by dividing forces associated with the urine's weight or pressure by the urine's specific gravity, as disclosed herein below. The circuitry may include a small printed circuit board (PCB) and/or a processor, which may be powered by a battery. The urine collection bag 120 and sensors 140 will be described further in the examples of FIGS. 2A-2C, catheter 110 will be described further in the examples of FIGS. 3A-3D, and details relevant to tubing 130 will be described further in the examples of FIGS. 4A-4B below.

In addition, system 100 can include a wireless transmission technology, such as BLUETOOTH® and/or Wi-Fi technology, to transmit the patient's UO data to an electronic medical records (EMR) system of a hospital or other facility. Of course, a wired connection may also be used in some embodiments.

The urine collection system 100 has a number of advantages over conventional methods and systems for measuring UO. In a typical embodiment, catheter 110 is external, so it poses lower risk of causing a catheter-associated urinary tract infection (CAUTI) than conventional indwelling Foley catheters. Further, as the urine collection bag 120 automatically measures the volume of urine, it eliminates human error that may occur when a nurse or other clinician visually measures the amount of UO in a collection container like a urine hat. System 100 can automatically transmit the UO data to an electronic medical records (EMR) system of a hospital or other facility, thereby saving time for clinicians because they do not need to measure patients' UO every hour. A clinician only needs to place catheter 110 once, and it can remain on the patient for the entire duration of the patient's stay. Moreover, system 100 virtually ensures patient compliance, by contrast with conventional systems, which require patients to urinate in a specific receptacle (such as a conventional urine hat or commode).

Figure 2A:
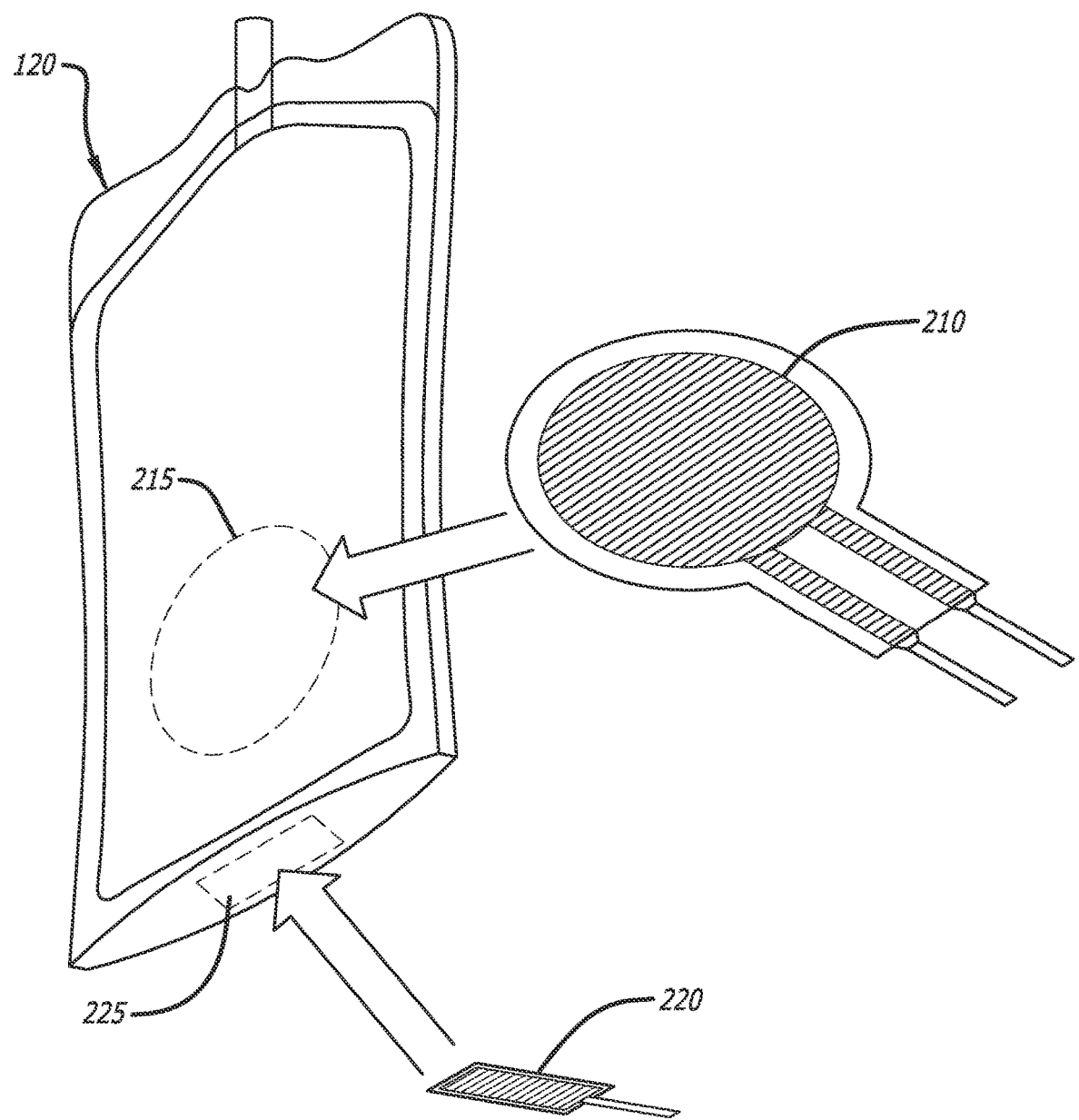
FIG. 2A displays details of a urine collection bag, according to some embodiments.

FIG. 2A displays the assembly 200 of the urine collection bag 120, according to some embodiments. In this example, the collection bag 120 contains a patient's urine, which can be measured by pressure sensor 210 on side wall 215 of collection bag 120, and/or by weight sensor 220, which may be located on a bottom or underside 225 of the collection bag 120. Sensors 210 and 220 can be coupled to or integrated into the urine collection bag 120, and are used to determine the amount of urine in bag 120. By automatically measuring the volume of urine, urine collection bag 120 improves accuracy and eliminates human error that may occur when a clinician visually measures the amount of UO in a conventional collection container, such as a urine hat.

In some embodiments, the urine collection bag 120 can include a network of multiple sensors located on the side 215 of and/or the underside 225 of the collection bag 120. In some embodiments, these multiple sensors can produce multiple force and/or pressure measurements that can be combined, either by simple averaging or by a more sophisticated algorithm or machine learning (ML) method. In some embodiments, the multiple sensors may operate synergistically such that collective information may be determined from the measurements/readings from a plurality of sensors that would otherwise be incomplete or unobtainable from just a single sensor. For example, the system 100 may determine which sensor readings are most reliable at any given time, e.g., as the collection bag 120 tilts, moves, and/or deforms during usage, and weight the individual sensor readings accordingly. In one example, such movement may be detected by a plurality of sensors 220 located on the underside 225 of the urine collection bag 120 when one or more sensors 220 measure a weight that differs from other sensors 220). In a second example, if the collection bag 120 tilts in a way such that sensor 210 no longer experiences pressure from the urine, or sensor 220 no longer experiences the weight of the urine, the system may temporarily reduce or eliminate its reliance on readings from those sensors.

In various embodiments, force sensors 210 and 220 may include one or more strain gauge sensors, pressure sensors, weight sensors, resistive elements, and the like, and are not limited by the present disclosure. All these specific forms of sensors may be referred to herein interchangeably as force sensors, or simply as sensors. In an embodiment, pressure sensor 210 may measure a pressure and/or strain exerted by side wall 215 due to the urine inside bag 120, as described in the example of FIG. 2B below. In an embodiment, weight sensor 220 directly measures the weight of urine in bag 120.

In some embodiments, little conversion is necessary from the pressure, weight, force, electrical resistance, and the like measured by sensors 210 or 220. For example, in the case of weight sensor 220, the sensor may measure the weight of the urine, which is a direct way to measure the quantity of UO. That is, the system may treat the force measurement of weight sensor 220 as a direct measurement of the amount of urine, for example by reporting the weight measurement of the urine (or the equivalent mass of the urine) directly to an EMR system of a hospital or other facility.

Alternatively, in some embodiments, conversion is necessary to determine the quantity of UO from the force sensor measurements. Accordingly, the system may include circuitry, such as a PCB and/or a processor powered by a battery, that can convert the measurements to a volume of urine based on the urine's specific gravity. For example, in the case of weight sensor 220, the circuitry may divide the weight, or the equivalent mass, by the urine's specific gravity or density to compute a volume. Likewise, in the case of pressure or strain sensor 210, the circuitry may need to compute the UO based on a measured pressure or strain on side wall 215 of collection bag 120. This may also be accomplished by dividing the measured force by the urine's specific gravity or density, as will be described further in the example of FIG. 2B below. Such conversion may be performed by hardware, firmware, and/or software implemented by the circuitry, PCB, and/or processors of the urine collection system, and is not limited by the present disclosure.

The specific gravity of the urine may be approximately 1.020, such as between 1.000 and 1.050, or more specifically between 1.010 and 1.030. In an embodiment, the system may receive the specific gravity as an input, for example from a nurse. The nurse may be able to change the specific gravity when needed, for example for use with a different patient, or when a patient's diet or health changes. In various embodiments, the system may receive the specific gravity via a user interface, or via Bluetooth or Wi-Fi technology from a local device, a local network, or an Internet cloud server. Patient-specific information, such as the specific gravity of the urine, may then be stored in transitory memory or non-transitory storage associated with urine collection bag 120 and/or the urine collection system, and is not limited by the present disclosure.

It should be noted that in some embodiments, the specific gravity of the collected urine may be determined based on at least the sensor measurements. In such embodiments, the circuitry of the system may determine and specific gravity of the collected urine and provide an alert or indication when the specific gravity is outside of a predetermined range. For example, a specific gravity outside of the range of 1.010 to 1.030 may indicate the patient's acute condition (e.g., dehydration) or a disease process progression (e.g., kidney failure).

Figure 2B:
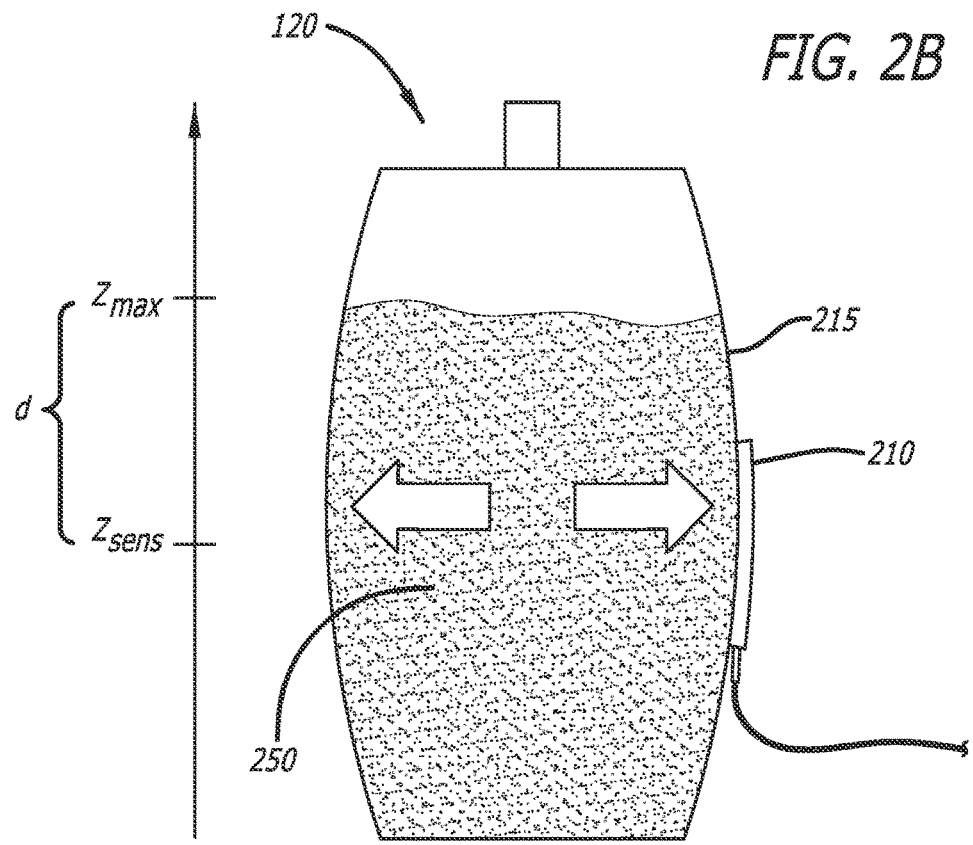
FIG. 2B displays the functioning of a force sensor in a urine collection bag, according to some embodiments.

FIG. 2B displays the functioning of a force sensor 210 located on a side wall 215 of urine collection bag 120, according to some embodiments. In this example, urine collection bag 120 is filled with urine 250, which exerts a pressure on side wall 215 of bag 120. Side wall 215 may expand and/or strain against force sensor 210. For example, in some embodiments, bag 120 is made of vinyl or another flexible material, so that side wall 215 can push against force sensor 210. In another example, bag 120 comprises a pouch, and as the bag fills, side wall 215 stretches or has an increased amount of pressure applied thereto.

In some embodiments, a countervailing force may be present on force sensor 210. Such a countervailing force may be necessary to stabilize force sensor 210, so that it does not accelerate or move, and can therefore measure the strain or pressure accurately. This force may be provided by various sources in various embodiments, for example from a stabilizing structure or element such as a fabric or elastic strap or reusable collection bag cover wrapped around the collection bag (see FIGS. 4A and 4B). Similarly, the countervailing force may be provided by an external surface, such as the patient's leg (see FIGS. 4A and 4B), another body part, or furniture such as a chair. In another example, the side walls 215 of collection bag 120 may themselves provide countervailing force to the pressure or strain from the urine, for example if side walls 215 are massive or stiff enough. In a related example, the force sensors may be contained within an internal layer of side walls 215 and/or collection bag 120 (see FIG. 2C). In the latter case, the exterior layer of side walls 215 and/or collection bag 120 may provide the countervailing force. In yet another example, bag 120 may be inside a rigid container that supports the bottom and walls of the bag, and moreover provides a countervailing force against the pressure of urine 250. Alternatively, the urine collection bag 120 may attach to a wheelchair, bed, or a patient's leg, which may also provide countervailing force. Accordingly, force sensor 210 can be stabilized so as to measure the strain or pressure exerted by the urine 250. The system then uses this measurement to determine the UO, as described herein below.

In various embodiments, the system's sensors, such as sensor 210, may include one or more strain gauge sensors, pressure sensors, weight sensors, resistive elements, and the like, and are not limited by the present disclosure. All these specific forms of sensors may be referred to herein interchangeably as force sensors. Force sensor 210 may comprise resistive elements with electrical resistance that changes in response to force. In particular, the force sensors may be strain gauge sensors, for example comprising piezoresistors or metallic foil elements that deform in response to strain, thereby changing the electrical resistance of the sensors. The change in the electrical resistance of sensor 210 may be measured by a printed circuit board (PCB), for example using a Wheatstone bridge, thereby measuring the force on sensor 210. In some embodiments, sensor 210 and the PCB may be powered by a battery and/or a rechargeable battery, so that the urine collection system is portable and convenient. The force sensors may be precise, for example they may be able to measure to within ±2 grams or ±0.02 Newtons, the accuracy needed for treating critical patients. Example force sensors include Model 1075 by Adafruit, Sensor-Puck by Silicon Labs, Model FSR06BE by Ohmite, and FSR 400 Series Force-Sensing Resistors by Interlink Electronics.

In some embodiments, the PCB and/or circuitry can also include Bluetooth and/or Wi-Fi technology to transmit the patient's UO data to an electronic medical records (EMR) system of a hospital or other facility. Such a feature can save time for clinicians because they do not need to measure patients' UO every hour.

In some embodiments, the system applies Bernoulli's equation to determine the variation of fluid pressure with depth, and/or to convert the force measurements to a volume of UO. For example, force measurement logic implemented by the circuitry, PCB, or processor can apply Bernoulli's equation to perform the conversion. Fluids such as water or urine, which has a similar specific gravity to water, may be approximately incompressible at typical room temperatures and ambient air pressures. Therefore, the system may apply a simplified form of Bernoulli's equation for an approximately incompressible fluid in equilibrium, i.e., with no net flow. In particular, Bernoulli's equation states that the pressure $P(z)$ varies as a function of height z in a column of incompressible fluid of density p because each layer of fluid must support all the fluid above it: $P(z)=P(z=0)-\rho g z$, where $P(z=0)$ is the pressure at the bottom of the column, and g=9.8 m/s² is the acceleration due to gravity. Note that the fluid's specific gravity is $\rho$ divided by the density $\rho_{H2O}$ of water. Defining $P(z=z_{max})$ as the pressure at the top $z_{max}$ of the column of fluid, and $d=z_{max}-z$ as the depth within the column, this is equivalent to $P(z)=P(z=z_{max})+\rho\ g\ d$.

Accordingly, if a pressure sensor 210 is located at a specific height $z_{sens}$ on the wall 215 of urine collection bag 120, it will experience an increase in pressure proportional to the amount $\rho$ d of fluid above $z_{sens}$. Specifically, setting $z_{max}$ as the top of the column of fluid, then $P(z=z_{max})=P_{atm}$ is atmospheric pressure, and the depth $d=z_{max}-z_{sens}$ is a measure of the amount of fluid above $z_{sens}$. Accordingly, the pressure P at depth d, the location of sensor 210, is increased over $P_{atm}$ by an amount $\rho$ g d proportional to the amount of fluid higher than sensor 210.

Note that this equation may remain correct even if side walls 215 are not vertical. Side walls 215 may not be vertical, both because collection bag 120 may itself have, for example, a convex shape, and because the pressure of the urine 250 may deform walls 215, particularly if the walls are made from a flexible material like vinyl. Thus, even though an incompressible fluid's density is constant, the lateral extent of the fluid at each height z may depend on z. If $z_{max}$ is located in a portion of the bag in which the bag's breadth increases with z, the fluid's top surface will still be unconstrained by the bag, and the above equations still hold for $z_{sens}$ below $z_{max}$. If $z_{max}$ is located in a portion of the bag in which the bag's breadth decreases with z, the depth d of fluid above $z_{sens}$ will vary with the lateral coordinates x and y, because at some locations the fluid's top surface is constrained by the bag walls. In equilibrium, the pressure P will still equilibrate at each height z in the fluid, and the bag walls will provide a force equivalent to the weight of the missing fluid. Accordingly, the pressure $P(z)$ is still $P(z_{max})+\rho\ g\ d$, where d is now measured from z to the highest point $z_{max}$ of the fluid at any lateral location (x, y). However, in the case of non-vertical walls, computing the volume of UO will require a correction for the expansion of the bag. In some embodiments, the system can model the bag's shape numerically. For example, the system may use interpolation based on empirical measurements of the bag's shape as a function of the volume of fluid.

In some embodiments, the force sensor does not require continuous calibration, because many commercially-available sensors, such as those mentioned above, are pre-calibrated. Force measurement logic implemented by the circuitry, PCB, or processor can be instructed to convert the measured pressure, force, or weight to volume of UO. In some embodiments, a single urine collection bag may be used for multiple patients in succession. In this case, it is preferable to perform a calibration check before using the urine collection bag with a new patient, so as to ensure the accuracy of the force sensor, and to ensure that the force sensor is still properly calibrated.

There are several ways the system can reduce or eliminate unwanted noise, such as spurious or stray forces on the bag, and prevent the noise from being recorded erroneously as UO. In some embodiments, a delay period can be implemented by the force measurement logic, so as to require at least a threshold period of quiet time before it records a force reading and converts this to a UO volume measurement. For example, suppose the force sensor senses a possibly transient mechanical impulse from the urine collecting into the bag 120. In fact, such a measured impulse could be due to new urine arriving in the bag 120, or to sloshing motion of the existing urine, or to any other transient noise source, and it may be difficult for the sensor to immediately differentiate among these scenarios. Accordingly, the force sensors and/or circuitry, PCB, or a processor associated with the urine collection bag 120 can be instructed to wait for the sensed force to stabilize, and remain substantially constant for a threshold period (e.g., 5, 10, or 15 seconds), before recognizing the force as a bonafide non-transient signal.

In some embodiments, noise can be filtered electronically so that only UO measurements are recorded. For example, the PCB can include a low pass RC filter to filter noise, which may originate in stray forces or in electronic noise within the circuit. For example, a low-pass RC filter with a cutoff frequency of 650 Hz may be used, such as a 750 ohm resistor and a 0.33 g capacitor. This filter may use a DC source impedance, which is generally compatible with a successive approximation analog-to-digital (A/D) converter of a microcontroller. This filter may be integrated into the PCB that controls the force sensors.

Figure 2C:
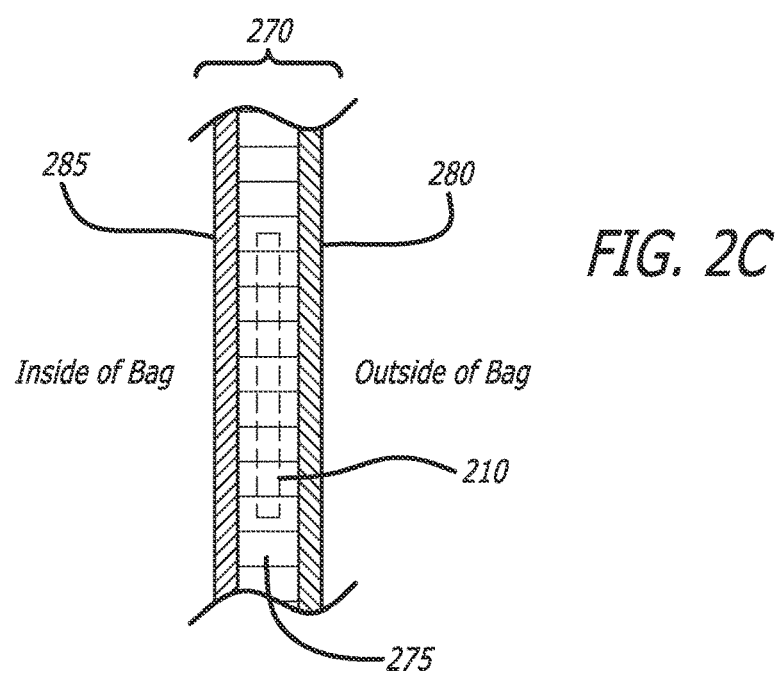
FIG. 2C displays a configuration of force sensors in a layer within the walls of a urine collection bag, according to some embodiments.

FIG. 2C displays a configuration of force sensors in a layer within the walls 270 of a urine collection bag, according to some embodiments. In this example, the force sensors can be integrated into a middle layer 275, sandwiched between exterior layer 280 and interior layer 285 of the urine collection bag. Interior layer 285 and exterior layer 280 can comprise a strong, flexible, watertight material, such as vinyl. Middle layer 275 may include all the instruments and/or electronics needed to measure the pressure or weight of the urine in the bag and to convert these measurements to the volume of UO. For example, middle layer 275 can include force sensor 210 of the example of FIG. 2B, circuitry, a PCB, and/or a processor. In an embodiment, the middle layer 275 can also include a battery to power the force sensors, circuitry, PCB, and/or processor. By containing all these elements in middle layer 275, the sandwich structure of wall 270 can protect sensitive instrumentation and/or electronics from the patient's urine, sweat, dirt, and any other contaminants. Moreover, the additional exterior side wall layer 280 can provide a countervailing force that stabilizes the force sensors in middle layer 275, making it possible to measure the pressure of the urine accurately. In an alternative embodiment, as described in the example of FIG. 2B, the force sensors may be outside the urine collection bag, and are not limited by the present disclosure.

Figure 3A:
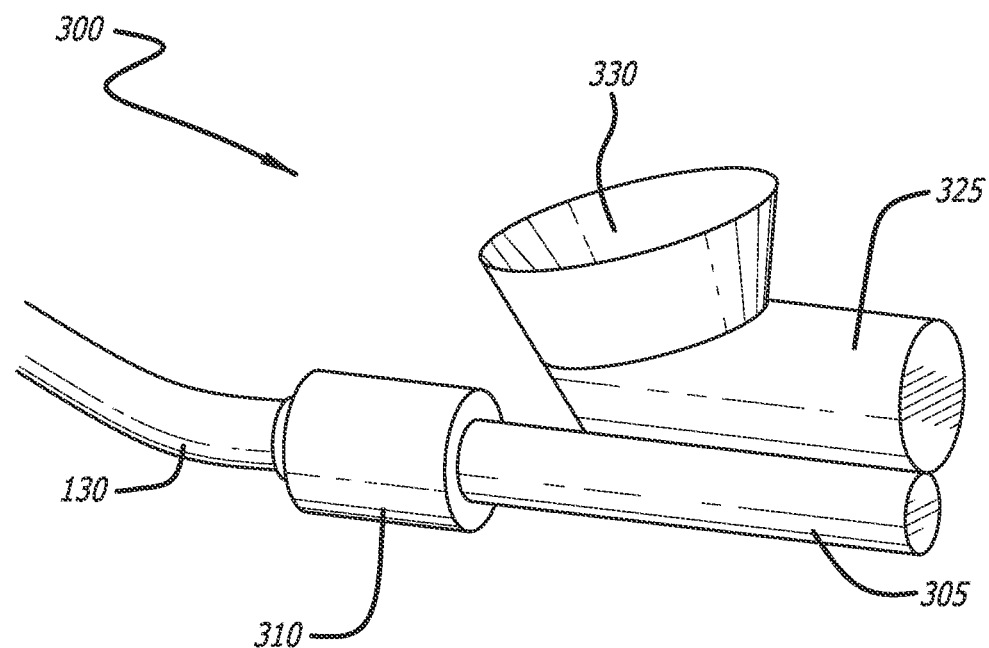
FIG. 3A illustrates details of a female external catheter (FEC), according to some embodiments.

The external catheter is also an important part of the urine collection system. Referring to FIG. 3A, details of a female external catheter (FEC) 300 are illustrated, according to some embodiments. FEC 300 includes coupled vessels 305 and 325, and can be connected via Luer connector 310 to drainage tubing 130, which leads to the urine collection bag. As shown, vessel 325 is curved upward to opening 330, which can receive urine from the patient's urethra. In an embodiment, the shape of the FEC 300 can be focused on coupling to the patient's urethra, and FEC 300 can be small and be held in place well due to its proximity to the patient anatomy.

In an embodiment, FEC 300 may be held in place by the female anatomy (for example, by the labia or an extension into the vaginal opening). In particular, the shape of FEC 300 can be designed to couple well enough to the patient anatomy, such that FEC 300 can remain in place and operational while the user comfortably lies down, sits (e.g., in a wheelchair, chair, or bed), stands, and even walks. Accordingly, a clinician only needs to place FEC 300, wicking catheter 340 (see FIG. 3B), finger-mountable catheter 360 (see FIG. 3C), or male external catheter 380 (see FIG. 3D) once, and it can remain on the patient for the entire duration of the patient's stay.

Because such external catheters are comfortable and can remain in place, the disclosed urine collection system virtually ensures patient compliance, by contrast with conventional systems, which require patients to urinate in a specific receptacle (such as a conventional urine hat or commode). Moreover, because FEC 300, wicking catheter 340, and finger-mountable catheter 360 are external, they pose lower risk of causing a CAUTI than an indwelling Foley catheter.

Figure 3B:
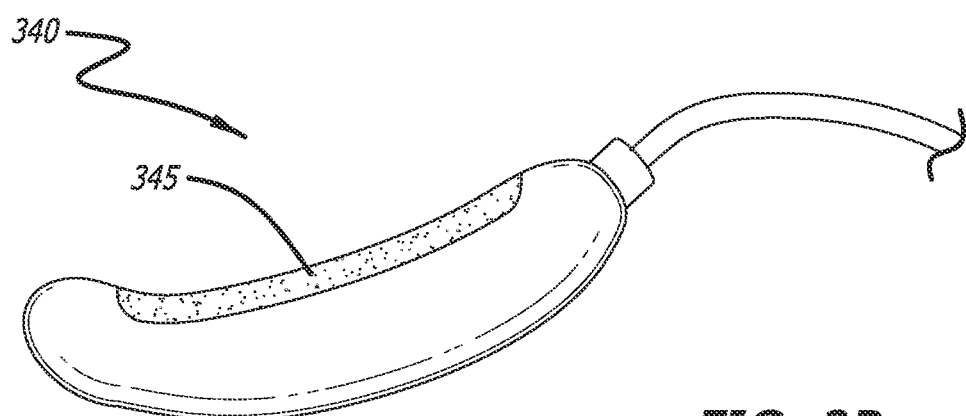
FIG. 3B illustrates details of a wicking catheter, according to some embodiments.

FIG. 3B illustrates details of a wicking catheter 340, according to some embodiments. Wicking catheter 340 has a wicking area 345, which may be comprised of gauze. In an example, wicking catheter 340 may be the PureWick (TM) catheter distributed by Bard Medical Devices. In some embodiments, wicking catheter 340 can be used together with a low pressure wall suction pump to wick urine gently away from the patient via wicking area 345, and into the urine collection bag. Alternatively, wicking catheter 340 may be an intermittent catheter, such as the intermittent catheters described in U.S. Provisional Application No. 63/060,615, filed Aug. 3, 2020, and titled "Intermittent-Catheter Assembly and Methods Thereof," and U.S. Provisional Application No. 63/077,469, filed Sep. 11, 2020, and titled "Intermittent-Catheter Assembly and Methods Thereof," each of which is incorporated by reference in its entirety into this application.

Figure 3C:
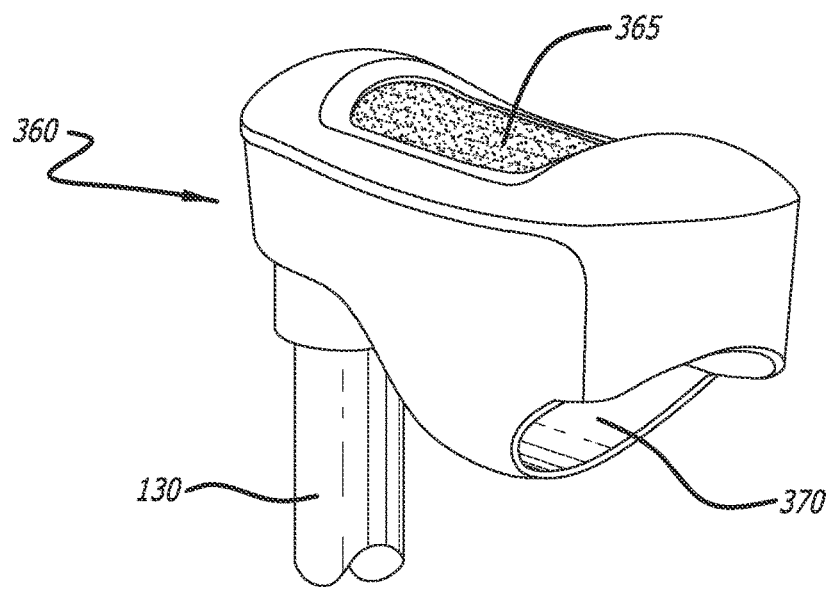
FIG. 3C illustrates details of a finger-mountable catheter, according to some embodiments.

FIG. 3C illustrates details of a finger-mountable catheter 360, according to some embodiments. In one example, finger-mountable catheter 360 also has a wicking area 365, which may be comprised of gauze. In addition, finger-mountable catheter 360 has a finger pocket 370 located on a bottom side of finger-mountable catheter 360. The finger pocket 370 may be a cavity that is configured to receive a user's finger. Once the user has inserted her finger into the finger pocket 370, she may manipulate the placement and orientation of finger-mountable catheter 360 such that wicking area 365 is placed over the patient's urethra in order to collect or "wick" urine, which is passed to the catheter tubing 130, and from there to the urine collection bag. Finger-mountable catheters are discussed further in U.S. Provisional Application No. 63/115,564, filed Nov. 18, 2020, and titled "External Catheter with Finger Pocket for Self-Placement," which is incorporated by reference in its entirety into this application.

Figure 3D:
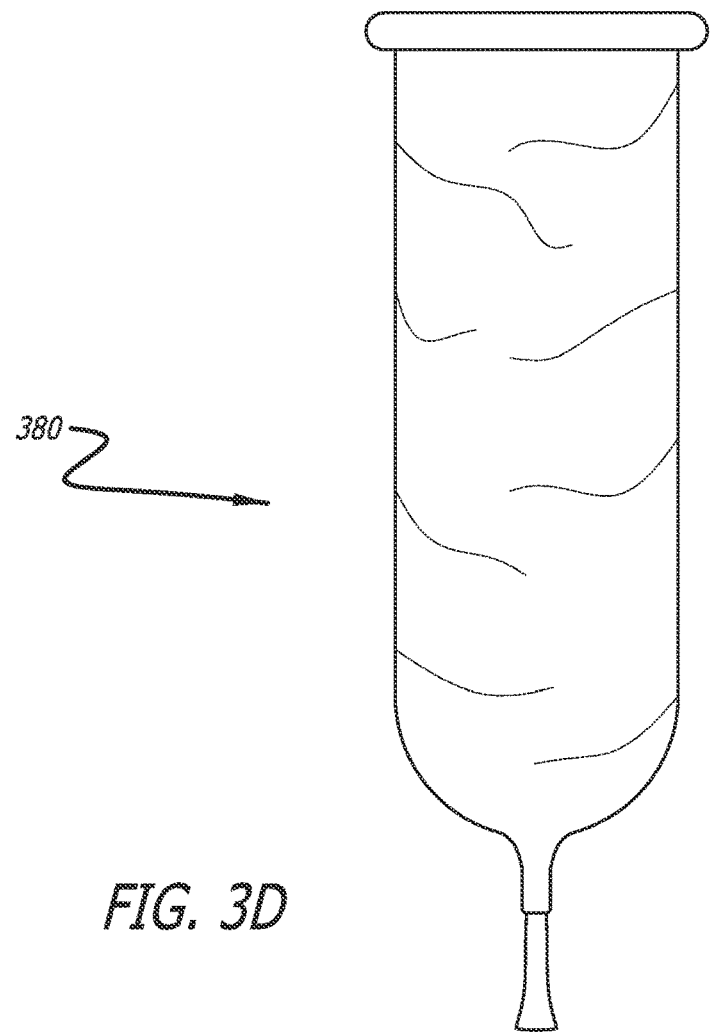
FIG. 3D illustrates details of a male external catheter (MEC), according to some embodiments.

FIG. 3D illustrates details of a male external catheter (MEC) 380, according to some embodiments. While the catheters of the examples of FIGS. 3A-3C above are female-only solutions, the disclosed system and methods can also be applied to males, for example using MEC 380, such as a so-called "condom-catheter." MEC 380 can also remain in place and operational while the user lies down, sits (e.g., in a wheelchair, chair, or bed), stands, and walks. In some embodiments, MEC 380 may include features to prevent leakage of urine, for example by improving directionality of flow or ameliorating gaps in the flow passage, thereby improving the accuracy of UO measured by the collection bag. Because MEC 380 is external, it poses a lower risk of causing a CAUTI than an indwelling Foley catheter.

The disclosed system addresses the need for clinicians to collect UO data, for the purpose of monitoring and adjusting the dosage of diuretics given to ambulatory patients, more accurately and less invasively than conventional systems. As described in the examples of FIGS. 3A-3D, the catheter can be designed to remain on a patient while the patient stands, walks, and goes about other activities. Accordingly, the disclosed system and methods can make accurate measurements of UO on a more continual basis than conventional systems, all while providing less disruption to patients' lives than conventional systems.

In some embodiments, the disclosed urine collection system can include means to secure and stabilize the urine collection bag. In particular, a reusable collection bag cover, fabric strap, or stabilization device that stabilizes the urine collection bag can be an important part of enabling the patient to go about normal activities, while fulfilling the need to monitor UO with very high accuracy.

Figure 4A:
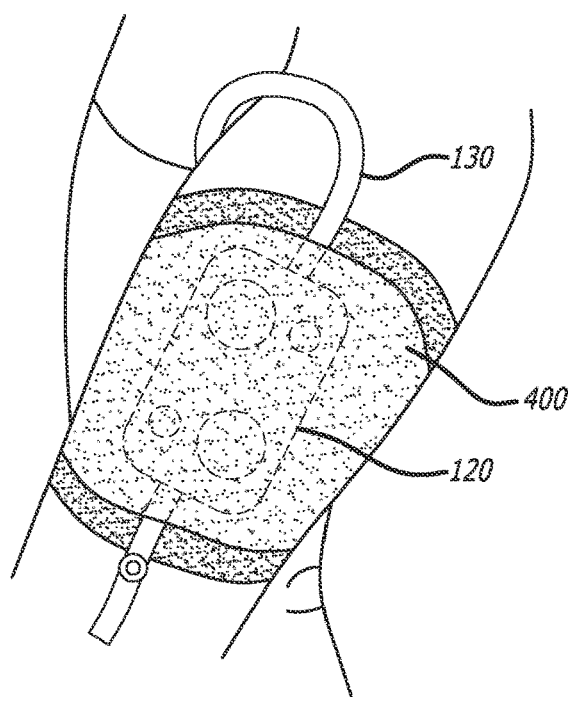
FIG. 4A illustrates a urine collection bag strapped to a patient's leg via a fabric strap, according to some embodiments.

Referring to FIG. 4A, a urine collection bag 120 strapped to a patient's leg via a fabric strap 400 is illustrated, according to some embodiments. In this example, the urine collection bag is placed on the patient's leg and is secured in place with fabric strap 400, which is wrapped around the patient's leg. Strap 400 can enable the patient to walk while wearing the catheter and collection bag, and while using the system to measure UO. Fabric strap 400 may also function as a reusable cover for the collection bag.

In an embodiment, the placement of the collection bag is not crucial to the system's operation, since the urine is collected from the patient by the catheter, and is then passed via the flexible drainage tubing 130 to the collection bag. Accordingly, key functions of strap 400 can be to secure the collection bag in proximity to the catheter, to conceal the urine in the collection bag, and to prevent the collection bag from shifting, spilling, being shaken, etc. However, in some embodiments, proper measurement of the UO may depend at least somewhat on satisfactory orientation or positioning of the collection bag. For example, it may be necessary to ensure the urine collection bag is not upside-down in order for the force sensors to measure force properly, particularly in the case where a sensor on the underside 225 of the collection bag measures the weight of the urine, such as sensor 225 in the example of FIG. 2A. In this case, the collection bag can be placed with the proper position and/or orientation, and secured with fabric strap 400.

In some embodiments, the fabric strap 400 may also contribute to the proper functioning of the collection bag, and in particular the force sensors. For example, as described in the example of FIG. 2B above, when urine flows into the collection bag, it can expand the collection bag so as to press against the force sensors. In an embodiment, the force sensors, or a PCB containing force sensors, can be located between the collection bag and fabric strap 400, which may be a reusable collection bag cover. Accordingly, fabric strap 400 may provide a countervailing force against the pressure from the urine in the collection bag. This countervailing force, in turn, may stabilize the force sensors and help obtain a more reliable force measurement. In an embodiment, the force sensors or PCB can be integrated into fabric strap 400. In an embodiment, the collection bag may be designed with layers, similar to the example of FIG. 2C, but fabric strap 400 may form an outer layer, rather than the outer vinyl layer 280 of FIG. 2C.

Tubing 130 may be flexible and durable enough to enable the patient to stand, walk, and perform normal activities comfortably, without damaging tubing 130. In some embodiments, tubing 130 may comprise plastic. For example, tubing 130 may be the same tubing used for conventional urine bags that are placed on a patient's leg.

Figure 4B:
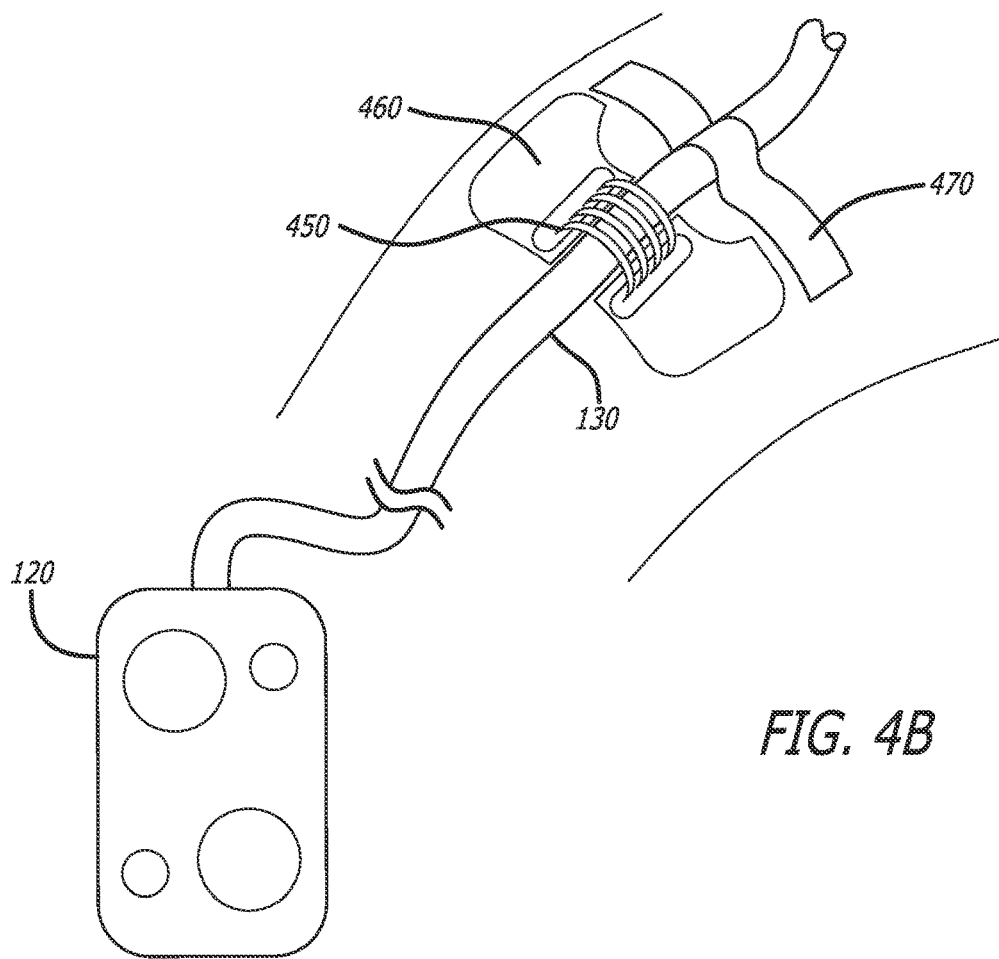
FIG. 4B illustrates a urine collection bag secured to a patient's leg via a stabilization device, according to some embodiments.

FIG. 4B illustrates flexible drainage tubing 130 of a urine collection system secured to a patient's leg via a stabilization device 450, according to some embodiments. In some embodiments, the flexible drainage tubing 130 is secured to the patient's leg with a stabilization device 450 comprising an adhesive pad and a retainer configured to stabilize the flexible drainage tubing 130. The adhesive pad can include one or more adhesive wings, for example two adhesive wings 460 as shown. In various embodiments, stabilization device 450 may be adhered and/or sutured to the patient's skin. Additional medical tape 470 may be used to secure the tubing 130. In an example, stabilization device 450 may be the STATLOCK® stabilization device distributed by C.R. Bard Inc. Stabilization device 450 has advantages over conventional stabilization methods, such as improved stability and retention, anatomical conformity, and adhesive strength. This can help ensure that the tubing 130 remains orderly and close to the patient, and reduces the risk of kinks, tangling, or breakage of tubing 130. In some embodiments, both fabric strap 400 and stabilization device 450 can be used together to stabilize both the collection bag and tubing 130.

Figure 5:
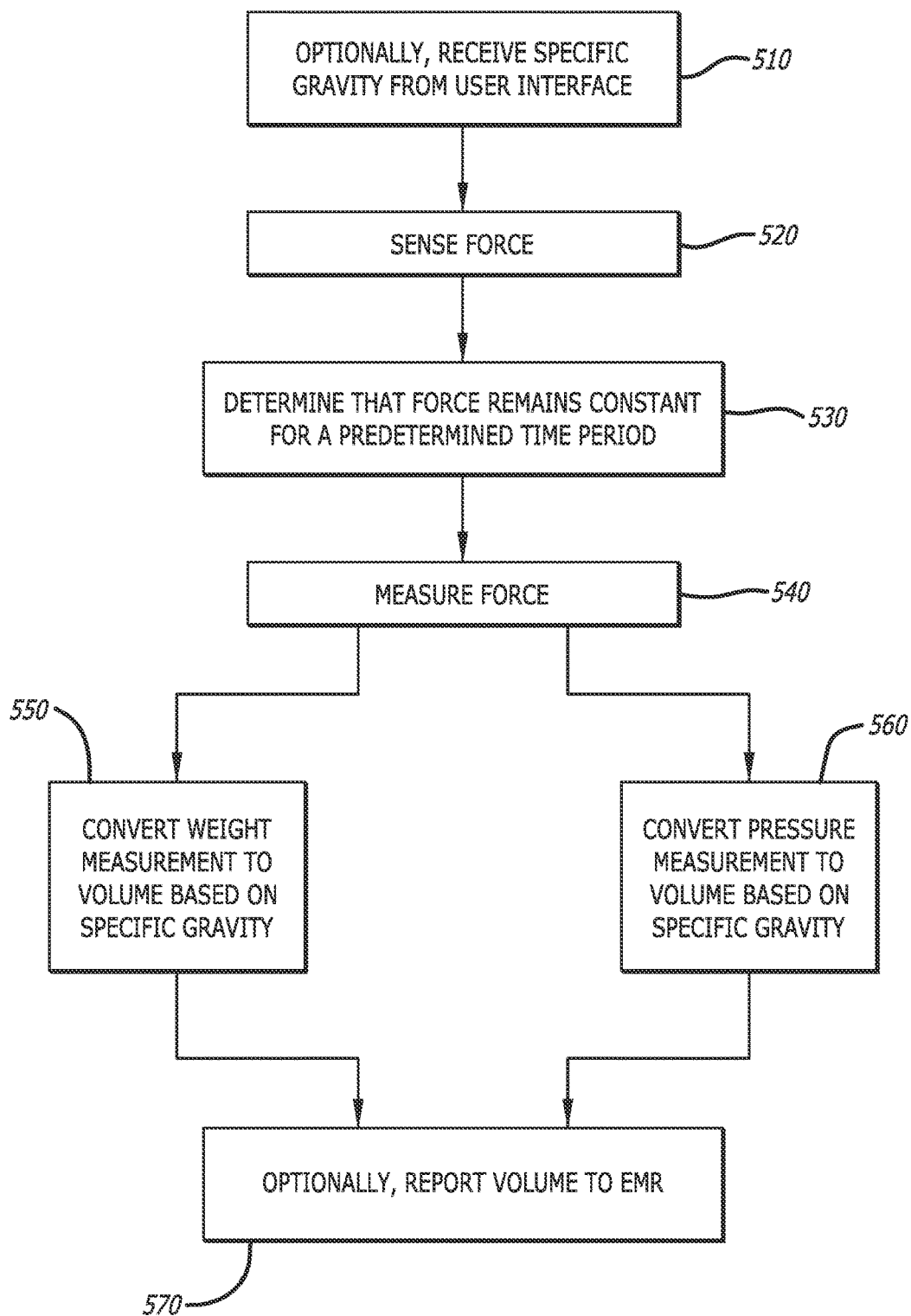
FIG. 5 shows a flowchart of an example method for measuring an amount of urine with a urine collection bag, according to some embodiments.

Referring to FIG. 5, a flowchart is shown of an example method 500 for measuring an amount of urine with a urine collection bag, according to some embodiments. Each block illustrated in FIG. 5 represents an operation performed in the method 500 of measuring an amount of urine with a urine collection bag. The method can be performed by a urine collection system, such as urine collection system 100 in the example of FIG. 1 above.

As an initial step in the method 500, the system can optionally receive the specific gravity as an input, for example from a clinician (block 510). The clinician may be able to input the specific gravity whenever needed, for example for use with a different patient, or when a patient's diet or health changes. In various embodiments, the system may receive the specific gravity via a user interface, or via a Bluetooth or Wi-Fi transmission from a local device, a local network, or an Internet cloud server. The system can subsequently use the specific gravity to compute the volume of UO based on force measurements. The specific gravity of the urine may be similar to that of water. For example, the specific gravity may be approximately 1.020, such as between 1.000 and 1.050, or more specifically between 1.010 and 1.030.

Next, the system can detect that a force is present (block 520). For example, the force sensors can detect a change in the pressure or weight of urine in the urine collection bag, as described in the example of FIG. 2B above. In some embodiments, the system can filter noise electronically so that only forces due to urine output are recorded. For example, a low-pass RC filter with a cutoff frequency of 650 Hz may be used, such as a 750 ohm resistor and a 0.33 µF capacitor. This filter may use a DC source impedance, which is generally compatible with a successive approximation analog-to-digital (A/D) converter of a microcontroller. This filter can be integrated into the PCB that controls the force sensors.

Next, the system can determine that the force remains substantially constant for a predetermined time period (block 530). In some embodiments, force measurement logic implemented by the circuitry, PCB, or processor requires at least a threshold delay period of quiet time before recording a force reading and converting this to a UO volume measurement. For example, suppose the force sensor senses a possibly transient mechanical impulse from the urine collecting into the bag 120. In fact, such a measured impulse could be caused by new urine arriving in the bag 120, by sloshing motion of the existing urine, or by some other transient noise source, and it may be difficult for the sensor to immediately differentiate among these scenarios. Accordingly, logic implemented by the force sensors and/or circuitry, PCB, or a processor associated with the urine collection bag can be instructed to wait for the sensed force to stabilize, and to remain substantially constant for a threshold period (e.g., 5 or 10 seconds), before recognizing the force as a bona-fide, non-transient signal.

In some embodiments, the system can record and/or transmit the UO measurement to an EMR system in response to an event, such as a detected change in the UO measurement. Accordingly, if the system detects a new force, and subsequently determines that the new force remains substantially constant for at least the threshold time period, it can record and/or transmit the UO measurement.

Having determined that the detected force is not noise and not transient, the system can measure the force using force sensors (block 540). In various embodiments, the system's force sensors may include one or more strain gauge sensors, pressure sensors, weight sensors, resistive elements, and the like, and are not limited by the present disclosure.

In some embodiments, a network of multiple force sensors can produce multiple force and/or pressure measurements that can be combined, either by simple averaging or by a more sophisticated algorithm or machine learning (ML) method. For example, the system may determine which sensor readings are most reliable at any given time, e.g., as the collection bag tilts, moves, and/or deforms during usage, and weight the individual sensor readings accordingly.

The force sensors may comprise resistive elements with electrical resistance that changes in response to force. In particular, the force sensors may be strain gauge sensors, for example comprising piezoresistors or metallic foil elements that deform in response to strain, thereby changing the electrical resistance of the sensors. The change in the electrical resistance of the sensors may be measured by a printed circuit board (PCB), for example using a Wheatstone bridge, thereby measuring the force on the sensors. In some embodiments, the sensors and the PCB may be powered by a battery and/or a rechargeable battery, so that the urine collection system is portable for a patient's convenient usage. The force sensors may be precise, for example they may be able to measure to within ±2 grams or ±0.02 Newtons, the accuracy needed for treating critical patients. Example force sensors include Model 1075 by Adafruit, Sensor-Puck by Silicon Labs, Model FSR06BE by Ohmite, and FSR 400 Series Force-Sensing Resistors by Interlink Electronics.

A countervailing force may be necessary to stabilize the force sensors, so that they do not accelerate or move, and can therefore measure the strain or pressure accurately. This force may be provided by various sources. For example, the side walls of the collection bag may themselves provide countervailing force to the pressure or strain from the urine, for example if side walls are massive or stiff enough. In a related example, the force sensors may be contained within an internal layer of the side walls and/or the collection bag (see FIG. 2C). In the latter case, the exterior layer of the side walls and/or the collection bag may provide the countervailing force. In another example, the countervailing force may be provided by an external surface, such as the patient's leg, or another body part (see FIGS. 4A and 4B). In yet another example, the countervailing force may be provided by a fabric or elastic strap or reusable collection bag cover wrapped around the collection bag (see FIG. 4A). Alternatively, the urine collection bag may attach to a chair, wheelchair, bed, or a patient's leg, which may provide the countervailing force.

Next, in the case that the force sensors have measured the weight of the urine in the collection bag, the system can convert this weight measurement to a UO volume based on specific gravity (block 550), for example by dividing the weight by the specific gravity or density of the urine. Alternatively, in the case that the force sensors have measured the pressure of the urine, the system can convert this pressure measurement to a UO volume based on specific gravity (block 560). In various embodiments, the system may receive the specific gravity via a user interface, or via Bluetooth or Wi-Fi technology from a local device, a local network, or an Internet cloud server. In some embodiments, force measurement logic implemented by the circuitry, PCB, or processor can perform the conversion in blocks 550 and 560.

In some embodiments, the system can apply Bernoulli's equation to determine the variation of fluid pressure with depth and/or to convert the force measurements to a volume of UO. For example, the circuitry of the urine collection system may divide the weight, or the equivalent mass, by the urine's specific gravity or density to compute a volume.

Finally, the system can optionally transmit the UO data to an electronic medical records (EMR) system of a hospital or other facility (block 570). For example, the EMR system can include detailed information about individual patients' UO, such as hourly or twice-hourly UO measurements. In various embodiments, the urine collection system can include Bluetooth and/or Wi-Fi technology, for example in the system's PCB and/or circuitry. In various embodiments, the system can use this technology to transmit the patient's measured UO data directly to a server maintaining the EMR or to transmit the UO data to a server over a network, such as a local-area network, a virtual private network, or the Internet. In various embodiments, the system can send updated UO data over a predetermined schedule, such as at regular intervals, or in response to particular events occurring, for example when the measured volume of urine changes by more than a threshold amount. This can save time for clinicians because they do not need to measure patients' UO every hour, or manually update the EMR or other records.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A urine collection bag configured to measure an amount of urine, the urine collection bag comprising:
    a collection area configured to collect the urine, wherein the urine is received via tubing from a catheter;
    multiple force sensors coupled to or integrated into the urine collection bag, the multiple force sensors configured to determine multiple force measurements of the urine collected within the collection area, the multiple force measurements corresponding to the multiple force sensors; and
    circuitry configured to determine the amount of the urine based a combination of the multiple force measurements, and a specific gravity of the urine,
    wherein the combination of the multiple force measurements includes an average of the multiple force measurements.

2. The urine collection bag of claim 1, wherein while determining the amount of the urine, the circuitry is further configured to:
    determine whether a force measured by the multiple force sensors remains substantially constant for a predetermined time period, and
    when a change in the force is detected, divide the force by the specific gravity of the urine to determine an increase of a volume of the urine.

3. The urine collection bag of claim 2, wherein the circuitry receives the specific gravity of the urine as an input via a user interface.

4. The urine collection bag of claim 1, wherein each of the multiple force sensors comprises a resistive element operative to change resistance in response to a force, and wherein the resistance is measured by a printed circuit board (PCB).

5. The urine collection bag of claim 4, wherein the PCB further comprises a low-pass filter operative to filter noise.

6. The urine collection bag of claim 1, wherein:
    the collection area comprises a flexible pouch, and
    the multiple force sensors measure a force of the urine by measuring an expansive force of the urine on one or more side walls of the flexible pouch.

7. The urine collection bag of claim 6, wherein the multiple force sensors are situated in an internal layer of the one or more side walls of the flexible pouch.

8. The urine collection bag of claim 1, wherein the catheter includes one or more of:
    a small female external catheter (FEC) with an opening disposed on a top side, the opening configured to couple to a female anatomical part,
    a wicking catheter having a wicking area disposed on a top side of the wicking catheter,
    a finger-mountable catheter having a finger cavity configured to receive a user finger on a bottom side of the finger-mountable catheter, or
    a male external catheter (MEC).

9. The urine collection bag of claim 8, wherein the catheter is configured to remain on a patient while the patient stands or walks.

10. The urine collection bag of claim 1, further comprising a wireless transmitter configured to transmit a determined amount of the urine to an electronic medical records system.

11. The urine collection bag of claim 1, wherein the circuitry comprises a printed circuit board (PCB) or a processor.

12. The urine collection bag of claim 1, wherein the multiple force sensors are powered by a battery.

13. A urine collection system comprising:
    a catheter;
    a urine collection bag configured to measure an amount of urine, the urine collection bag comprising:
        a collection area configured to collect the urine, wherein the urine is received via flexible drainage tubing from the catheter,
        multiple force sensors coupled to or integrated into the urine collection bag, the multiple force sensors configured to determine multiple force measurements of the urine collected within the collection area, the multiple force measurements corresponding to each of the multiple force sensors, and
        circuitry configured to determine:
            the amount of the urine based on at least one of the multiple force measurements corresponding to one of the multiple force sensors and a specific gravity of the urine, a difference between different force measurements of the multiple force measurements corresponding to different force sensors of the multiple force sensors, and at least one of tilting, movement, or deformation of the urine collection bag based on the difference; and the flexible drainage tubing coupling the catheter to the urine collection bag.

14. The urine collection system of claim 13, wherein the flexible drainage tubing is configured to be secured to a leg of a patient with either:

a stabilization device comprising:
an adhesive pad comprising one or more adhesive wings; and
a retainer configured to stabilize the flexible drainage tubing, or a fabric strap configured to be wrapped around the leg.

15. The urine collection system of claim 13, wherein while determining the amount of the urine, the circuitry is further configured to:

determine whether a force measured by the multiple force sensors remains substantially constant for a predetermined time period, and when a change in the force is detected, divide a pressure by the specific gravity of the urine to determine an increase of a volume of the urine.

16. The urine collection system of claim 15, wherein the circuitry receives the specific gravity of the urine as an input via a user interface.

17. The urine collection system of claim 13, wherein each of the multiple force sensors comprises a resistive element operative to change resistance in response to a force, and further comprising a printed circuit board (PCB) configured to measure the resistance.

18. The urine collection system of claim 17, wherein the PCB further comprises a low-pass filter operative to filter noise.

19. The urine collection system of claim 14, wherein:
the collection area of the urine collection bag comprises a flexible pouch, and
the multiple force sensors measure a force of the urine by measuring an expansive force of the urine on one or more side walls of the flexible pouch.

20. The urine collection system of claim 19, wherein the multiple force sensors are situated in an internal layer of the one or more side walls of the flexible pouch.

21. The urine collection system of claim 13, wherein the catheter includes one or more of:

a small female external catheter (FEC) with an opening disposed on a top side, the opening configured to couple to a female anatomical part, a wicking catheter having a wicking area disposed on a top side of the wicking catheter, a finger-mountable catheter having a finger cavity configured to receive a user finger on a bottom side of the finger-mountable catheter, or a male external catheter (MEC).

22. The urine collection system of claim 21, wherein the catheter is configured to remain on a patient while the patient stands or walks.

23. The urine collection system of claim 13, further comprising a wireless transmitter configured to transmit a determined amount of the urine to an electronic medical records system.

24. The urine collection system of claim 13, wherein the circuitry comprises a printed circuit board (PCB) or a processor.

25. The urine collection system of claim 13, wherein multiple force sensors are powered by a battery.

* * * * *